United States Patent [19]
Zetter et al.

[11] Patent Number: 6,150,117
[45] Date of Patent: Nov. 21, 2000

[54] METHOD FOR DIAGNOSIS OF CANCER

[75] Inventors: Bruce R. Zetter, W. Newton; Lere Bao, Brookline, both of Mass.

[73] Assignee: Children's Medical Center Corporation, Boston, Mass.

[21] Appl. No.: 09/135,599

[22] Filed: Aug. 18, 1998

Related U.S. Application Data

[62] Division of application No. 08/664,857, Jun. 17, 1996, Pat. No. 5,858,681.

[51] Int. Cl.$^7$ .......................... G01N 33/53; G01N 33/48; C12Q 1/68; C12P 19/34
[52] U.S. Cl. .............................. 435/7.1; 435/6; 435/91.1; 435/91.2; 435/91.21; 435/7.23; 435/40.52
[58] Field of Search ................................ 435/7.1, 6, 91.1, 435/91.2, 91.21, 7.23, 40.52

*Primary Examiner*—Susan Ungar
*Attorney, Agent, or Firm*—Nixon Peabody LLP

[57] ABSTRACT

The present inventors have discovered that humans have a gene that encodes a novel protein of the thymosin β family. This novel protein, herein referred to as thymosin β15, has the ability to bind and sequester G-actin, like other members of the thymosin β family, but unlike what is known about other members also directly regulates cell motility in prostatic carcinoma cells. A cDNA of the human thymosin β15 gene (SEQ ID NO: 1) and having the deduced the amino acid sequence (SEQ ID NO: 2) was isolated. The present inventors have shown that enhanced transcripts (mRNA) and expression of the thymosin β15 gene in non-testicular cells has a high correlation to disease state in a number of cancers, such as prostate, lung, melanoma and breast cancer, particularly metastatic cancers. Accordingly, discovering enhanced levels of transcript or gene product in non-testicular tissues can be used in not only a diagnostic manner, but a prognostic manner for particular cancers.

6 Claims, 5 Drawing Sheets

FIG. 1

```
TATCAGCTAG TGGCTGCACC CGGAACACC ACCCTGGTCC GGAGTAGCTG CGGACAGAAT      60

TGCTGGCCTA GTAGAAGCTT TGGAACGAGC AGTCAAG ATG AGT GAT AAA CCA GAC    115
                                         M   S   D   K   P   D

TTA TCA GAA GTT GAA ACA TTT GAC AAA TCA AAG TTG AAG AAG ACT AAT      163
 L   S   E   V   E   T   F   D   K   S   K   L   K   K   T   N
 1

ACT GAA GAA AAG AAT ACT CTT CCT TCG AAG GAA ACT ATC CAG CAG GAG      211
 T   E   E   K   N   T   L   P   S   K   E   T   I   Q   Q   E

AAA GAA TAT AAT CAA AGA TC ATAAAATGAG ATTCTCCTCT CAAGAGCAAC TTCAAC   267
 K   E   T   N   Q   R   S   *

TTTGCTGGAT AGTCTTGGAT TTAGACATGT TTCTGTAAAC CTATCCAATA TGTAGACATT    327
TTAGGCGGTT CCTGATAGGT TCTTAAGTAC CCTGACTGAA AGTCAGCAT TTAACACCAA     387
TCATTAAATG TGTTTTCCAC TGCTC                                          412
```

FIG. 2

```
Ratthymb4      .MSDKPDMAE IIEKFDKSKLE KTEQEKNPL PSKETIEQEK QAGES.....   49
Bovthymb9      .AQADKPDLGE INSFDKAKLE KTETQEKNTL PTKETIEQEK QAK.......   50
Ratthymb10     .MADKPDMGE ILASFDKAKLE PTKETIEQEK QAK.......              49
Troutthymb11   .ACSDKPNLEE VASFDKTKLE KTETQEKNTL PTKETIEQEE RSETS.....   50
Troutthymb12   ACSDKPDLAE VSNMFDKTKLE KTETQEKNPL PTKETIEQEE QAS.......   50
Humanthymb15   .MSDKPDLSE VETFDKSKLE KINTEEKNTL PSKETIQQEK EYNQRS....     49
```

METHOD FOR DIAGNOSIS OF CANCER

This Application is a divisional of U.S. patent application 08/664,857, filed Jun. 17, 1996, now U.S. Pat. No. 5,858,681.

The work described herein was supported, in part, by National Institutes of Health grant CA37393. The U.S. Government has certain rights to this invention.

BACKGROUND OF THE INVENTION

The present invention provides methods for diagnosing cancer, particularly metastatic cancer.

The increased number of cancer cases reported around the world is a major concern. There are currently only a few treatments available for specific types of cancer, and these provide no absolute guarantee of success. Most treatments rely on an approach that involves killing off rapidly growing cells in the hope that rapidly growing cancerous cells will succumb, either to the treatment, or at least be sufficiently reduced in numbers to allow the body's system to eliminate the remainder. Moreover, many of these treatments adversely effect non-malignant cells. Consequently, an appreciation of the severity of the condition must be made before beginning many therapies. In order to most effective, these treatments require not only an early detection of the malignancy, but an appreciation of the severity of the malignancy.

While different forms of cancer have different properties, one factor which many cancers share is that, in order to be fatal, they must metastasize. Until such time as metastasis occurs, a tumor, although it may be malignant, is confined to one area of the body. This may cause discomfort and/or pain, or even lead to more serious problems, but if it can be located, it may be surgically removed and, if done with adequate care, cause no further problems. However, once metastasis sets in, cancerous cells have invaded the body and while surgical resection may remove the parent tumor, this does not address other tumors. Only chemotherapy, or some particular form of targeting therapy, then stands any chance of success.

The process of tumor metastasis is a multistage event involving local invasion and destruction of intercellular matrix, intravasation into blood vessels, lymphatics or other channels of transport, survival in the circulation, extravasation out of the vessels in the secondary site and growth in the new location (Fidler, et al., *Adv. Cancer Res.* 28, 149–250 (1978), Liotta, et al., *Cancer Treatment Res.* 40, 223–238 (1988), Nicolson, *Biochim. Biophy. Acta* 948, 175–224 (1988) and Zetter, *N. Eng. J. Med.* 322, 605–612 (1990)). Success in establishing metastatic deposits requires tumor cells to be able to accomplish these steps sequentially. Common to many steps of the metastatic process is a requirement for motility. The enhanced movement of malignant tumor cells is a major contributor to the progression of the disease toward metastasis. Increased cell motility has been associated with enhanced metastatic potential in animal as well as human tumors (Hosaka, et al., *Gann* 69, 273–276 (1978) and Haemmerlin, et al., *Int. J. Cancer* 27, 603–610 (1981)).

Tumor angiogenesis is essential for both primary tumor expansion and metastatic tumor spread, and angiogenesis itself requires ECM degradation (Blood et al., *Biochim. Biophys. Acta* 1032:89–118 (1990)). Thus, malignancy is a systemic disease in which interactions between the neoplastic cells and their environment play a crucial role during evolution of the pathological process (Fidler, I. J., *Cancer Metastasis Rev.* 5:29–49 (1986)).

Identifying the alterations in gene expression which are associated with malignant tumors, including those involved in tumor progression, is clearly a prerequisite not only for a full understanding of cancer, but also to develop new rational therapies against cancer.

A further problem arises, in that the genes characteristic of cancerous cells are very often host genes being abnormally expressed. It is quite often the case that a particular protein marker for a given cancer while expressed in high levels in connection with that cancer is also expressed elsewhere throughout the body, albeit at reduced levels.

Prostatic carcinoma is the most prevalent form of cancer in males and the second leading cause of cancer death among older males (Boring, et al., *Cancer J. Clinicians,* 7–26 (1994)). Clinically, radical prostatectomy offers a patient with locally contained disease an excellent chance for cure. Unfortunately, if diagnosed after metastases are established, prostatic cancer is a fatal disease for which there is no effective treatment to significantly increase survival. Recent advances in prostatic cancer diagnosis has allowed the earlier detection of human prostate cancer by use of the PSA test (Catalona, et al., *J. Urol.*, 151, 1283–1290 (1994)). Unfortunately, this early detection has not been accompanied by an improvement in determining which tumors may progress to the metastatic stage (Cookson, et al., *J. Urology* 154, 1070–1073 (1995) and Aspinall, et al., *J. Urology* 154, 622–628 (1995)). Since many individuals having prostate cancer are not adversely effected by the cancer, considerable controversy has arisen as to the use of such tests. Thus, methods for early detection and early appreciation of the potential for or of the severity of the cancer, that can be taken into account in treatment of, for example, metastatic disease are desirable.

Bao and Zetter reported in an abstract presented at the American Association for Cancer Research annual meeting (Mar. 18–22, 1995) the differential expression of a novel mRNA expressed in high-metastatic rat tumor cell lines, but not in a low metastatic variant. cDNA was isolated and was reported to encode a protein with 68% identity to the rat thymosin β4. However, the nucleotide sequence and the deduced amino acid sequence were not reported.

SUMMARY OF THE INVENTION

We have now discovered that humans have a gene that encodes a novel protein of the thymosin β family. This novel protein, herein referred to as thymosin β15, has the ability to bind and sequester G-actin, like other members of the thymosin β family, but unlike what is known about other members also directly regulates cell motility in prostatic carcinoma cells. We have isolated a cDNA of the human thymosin β15 gene (SEQ ID NO: 1) and have deduced the amino acid sequence (SEQ ID NO: 2). We have shown that enhanced transcripts (mRNA) and expression of the thymosin β15 gene in non-testicular cells has a high correlation to disease state in a number of cancers, such as prostate, lung, melanoma and breast cancer, particularly metastatic cancers. Accordingly, discovering enhanced levels of transcript or gene product in non-testicular tissues can be used in not only a diagnostic manner, but a prognostic manner for particular cancers.

In a first aspect the present invention provides a method of diagnosing cancer, especially prostate, lung, melanoma and breast cancer, in a patient by measuring levels of thymosin β15 in a biological specimen obtained from the patient. Levels of thymosin β15 in the sample greater than a base line level is indicative of cancer. Biological specimens include, for example, blood, tissue, serum, stool, urine, sputum, cerebrospinal fluid and supernatant from cell lysate. Preferably, one uses tissue specimens. The determination of base lines and comparison levels is by standard modes of analysis based upon the present disclosure.

In another aspect, the present invention provides a method of prognosis in an individual having cancer, especially prostate, lung, melanoma and breast cancer, by measuring levels of thymosin β15 in a tumor sample obtained from a patient to be tested. Expression of thymosin β15 in said tumor sample greater than a base line level for that particular tissue indicates a higher risk of tumor metastasis.

In yet another aspect, the present invention provides a method for determining the metastatic potential of a tumor by measuring the level of thymosin β15 expression in the tumor. Expression of thymosin β15 in said tumor greater than a base line level for that particular tissue indicates an increased metastatic potential.

In yet another embodiment, changes in condition can be monitored by comparing changes in thymosin β15 expression levels in the tumor in that subject over time.

In the methods of the present invention, levels of thymosin β15 can be ascertained by measuring the protein directly or indirectly by measuring transcript (mRNA) encoding thymosin β15. mRNA levels can be measured, for example, using an RNA dependent polymerase chain reaction, e.g., reverse transcriptase PCR, or Northern blot analysis.

Base line levels can readily be determined by measuring levels of thymosin β15 in sample of disease free individuals.

The present invention also provides of a method for measuring human thymosin β15 levels using an antibody or antibody fragment which selectively binds human thymosin β15. This method comprises the steps of:

a. contacting a sample or preparation thereof with an antibody or antibody fragment which selectively binds human thymosin β15, and
b. detecting whether said antibody or said antibody fragment is bound by said sample and thereby measuring the levels of human thymosin β15 present, wherein a negative result is indicative of a better prognosis than a positive result.

The term "unique fragment" refers to a portion of the nucleotide sequence or polypeptide of the invention that will contain sequences (either nucleotides or amino acid residues) present in thymosin β15 (SEQ ID NO: 2) but not in other members of the thymosin family. This can be determined when the hybridization profile of that fragment under stringent conditions is such that it does not hybridize to other members of the thymosin family. Such fragments can be ascertained from FIG. 2. A preferred set of unique fragments are those that contain, or contain polynucleotides that encode, amino acid 7 to 12 of SEQ ID NO: 2, amino acid 21 to 24 of SEQ ID NO: 2 and amino acid 36 to 45 of SEQ ID NO: 2. Preferably, the unique nucleotide sequence fragment is 10 to 60 nucleotides in length, more preferably, 20 to 50 nucleotides, most preferably, 30 to 50 nucleotides. Preferably, the unique polypeptide sequence fragment is 4 to 20 amino acids in length, more preferably, 6 to 15 amino acids, most preferably, 6 to 10 amino acids.

DESCRIPTION OF THE DRAWINGS

FIG. 1 is the nucleotide sequence (SEQ ID NO: 1) of T,β15 cDNA and the predicted amino acid sequence (SEQ ID NO: 2) (single-letter code). The sequence numbers of the nucleotides and amino acids are indicated on the right side of the sequences. The translation initiation codon ATG is underlined, and the termination codon TAA is marked with an asterisk. A putative actin binding region is underlined. These sequence data are available from GenBank under accession number U25684.

FIG. 2 shows the alignment of the deduced Tβ15 protein sequence and some of the others β thymosin isoforms. Regions of amino acid identity are represented by white letters boxed in black. Unboxed black letters correspond to nonidentical regions. Dots correspond to gaps introduced in the sequence to optimize alignment.

FIG. 3A shows differential expression in tumors. The small arrow shows positive staining. The large arrow shows negative staining. FIG. 3B shows that in poorly differentiated and invasive prostate carcinoma, single cells invading stroma display intense staining (arrow).

FIG. 4A. Vector control transfected (o, ▽) and Tβ15 antisense (●, ▼) transfected AT3.1 cell clones. FIG. 4B. Vector control transfected (o, ▽) and Tβ15 sense transfected (●, ▼) AT2.1 cell clones. Data are expressed as the mean ±SE (n=4). FIG. 4C. Growth curves of control transfected and Tβ15 (sense or antisense) transfected Dunning R-3327 clones. Cells from vector control transfected AT2.1 (o), Tβ15 sense transfected AT2.1 (●), vector control transfected AT3.1 (o) and Tβ15 antisense transfected AT3.1 (▼) were plated at initial $10^4$ cells/well in RPMI 1640 with 10% FBS and 250 nM dexamethasone in 12-well plates. Cells were harvested and counted at indicated times. Points represent the mean ±SE (n=3).

DETAILED DESCRIPTION OF THE INVENTION

Figure 3A:
FIGS. 3A and 3B show in situ hybridization with antisense riboprobe for Tβ15 on prostatic adenocarcinoma patients.

Although members of the thymosin β family have been shown to bind and sequester G-actin, they have not previously been demonstrated to alter cell motility. Our studies, however, reveal that thymosin β15 directly regulates cell motility in prostatic carcinoma cells. We have shown that expression of thymosin β15 is upregulated in highly metastatic prostate cancer cell lines relative to poorly metastatic or nonmetastatic lines. In addition, thymosin β15 was expressed in human prostate carcinoma specimens but not in normal human prostate. Although not wishing to be bound by theory, this indicates that β15 plays a role in the process of metastatic transformation.

Accordingly, the evaluation and comparison of levels of transcript (mRNA) or gene product, either normal or mutated, in non-testicular tissue can be both diagnostic and prognostic of particular cancer. For example, an elevated level is indicative of a greater tendency for metastatic activity. Further, by monitoring a particular neoplastic growth over a period of time and comparing changes in level one can evaluate changes in metastatic activity. The level of β15 can also be used to determine the severity of a particular tumor. We have found that β15 expression correlates with gradations of tumor severity. For example, the expression of β15 in prostate cells is well correlated with the Gleason grade of prostate carcinoma.

The present invention provides a method of diagnosing cancer, especially prostate, lung, melanoma and breast cancer, in a patient by measuring levels of thymosin β15 in a biological specimen obtained from the patient. Levels of thymosin β15 in the sample greater than a base line level is indicative of cancer. Base line levels can readily be determined by measuring levels of thymosin β15 in sample of disease free individuals.

Biological specimens include, for example, blood, tissue, serum, stool, urine, sputum, cerebrospinal fluid and supernatant from cell lysate. Preferably, one uses tissue specimens. The determination of base lines and comparison levels is by standard modes of analysis based upon the present disclosure.

The present invention also provides a method of prognosis in an individual having cancer, especially prostate, lung, melanoma and breast cancer, by measuring levels of thymosin β15 in a tumor sample obtained from a patient to be tested. Expression of thymosin β15 in said tumor sample greater than a base line level for that particular tissue indicates a higher risk of tumor metastasis. This information can be used by the physician in determining the most effective course of treatment.

Changes in a patients condition can be monitored using the methods of the present invention by comparing changes in thymosin β15 expression levels in the tumor in that subject over time.

The present invention further provides a method for determining the metastatic potential of a tumor by measuring the level of thymosin β15 expression in the tumor. Expression of thymosin β15 in said tumor greater than a base line level for that particular tissue indicates an increased metastatic potential.

Standard detection techniques well known in the art for detecting RNA, DNA, proteins and peptides can readily be applied to detect thymosin β15 or its transcript to diagnose cancer, especially metastatic cancer or to confirm that a primary tumor has, or has not, reached a particular metastatic phase.

Such techniques may include detection with nucleotide probes or may comprise detection of the protein by, for example, antibodies or their equivalent. Preferably, the nucleotide probes may be any that will hybridize more strongly to the sequence shown in SEQ ID NO: 1 than to other naturally occurring thymosin sequences. Types of probe include cDNA, riboprobes, synthetic oligonucleotides and genomic probes. The type of probe used will generally be dictated by the particular situation, such as riboprobes for in situ hybridization, and cDNA for Northern blotting, for example. The most preferred probes are those which correspond to the DNA of SEQ ID NO: 1. Preferably the probe is directed to the thymosin β15 coding region, i.e., nucleotides 98–232 of SEQ ID NO: 1. Most preferably, the probe is directed to nucleotide regions unique to thymosin β15, e.g., nucleotides 113–133, 158–169 or 200–232 of SEQ ID NO: 1. Detection of the thymosin β15 encoding gene, per se, will be useful in screening for mutations associated with enhanced expression. Other forms of assays to detect targets more readily associated with levels of expression—transcripts and other expression products will generally be useful as well. The probes may be as short as is required to differentially recognize thymosin β15 mRNA transcripts, and may be as short as, for example, 15 bases.

A probe may also be reverse-engineered by one skilled in the art from the amino acid sequence of SEQ ID NO:2. However use of such probes may be limited, as it will be appreciated that any one given reverse-engineered sequence will not necessarily hybridize well, or at all with any given complementary sequence reverse-engineered from the same peptide, owing to the degeneracy of the genetic code. This is a factor common in the calculations of those skilled in the art, and the degeneracy of any given sequence is frequently so broad as to yield a large number of probes for any one sequence.

The form of labelling of the probes may be any that is appropriate, such as the use of radioisotopes, for example, $^{32}$P and $^{35}$S. Labelling with radioisotopes may be achieved, whether the probe is synthesized chemically or biologically, by the use of suitably labelled bases. Other forms of labelling may include enzyme or antibody labelling such as is characteristic of ELISA.

Detection of RNA transcripts may be achieved by Northern blotting, for example, wherein a preparation of RNA is run on a denaturing agarose gel, and transferred to a suitable support, such as activated cellulose, nitrocellulose or glass or nylon membranes. Radiolabelled cDNA or RNA is then hybridized to the preparation, washed and analyzed by autoradiography.

In situ hybridization visualization may also be employed, wherein a radioactively labelled antisense cRNA probe is hybridized with a thin section of a biopsy sample, washed, cleaved with RNase and exposed to a sensitive emulsion for autoradiography. The samples may be stained with haematoxylon to demonstrate the histological composition of the sample, and dark field imaging with a suitable light filter shows up the developed emulsion. Non-radioactive labels such as digoxigenin may also be used.

Immunohistochemistry may be used to detect expression of human thymosin β15 in a biopsy sample. A suitable antibody is brought into contact with, for example, a thin layer of cells, washed, and then contacted with a second, labelled antibody. Labelling may be by enzyme, such as peroxidase, avidin or by radiolabelling. Chromogenic labels are generally preferable, as they can be detected under a microscope.

More generally preferred is to detect the protein by immunoassay, for example by ELISA or RIA, which can be extremely rapid. Thus, it is generally preferred to use antibodies, or antibody equivalents, to detect thymosin β15.

It may not be necessary to label the substrate, provided that the product of the enzymatic process is detectable and characteristic in its own right (such as hydrogen peroxide for example). However, if it is necessary to label the substrate, then this may also comprise enzyme labelling, labelling with radioisotopes, antibody labelling, fluorescent marker labelling or any other suitable form which will be readily apparent to those skilled in the art.

Antibodies may be prepared as described below, and used in any suitable manner to detect expression of thymosin β15. Antibody-based techniques include ELISA (enzyme linked immunosorbent assay) and RIA (radioimmunoassay). Any conventional procedures may be employed for such immunoassays. The procedures may suitably be conducted such that: a thymosin β15 standard is labelled with a radioisotope such as $^{125}$I or $^{35}$S, or an assayable enzyme, such as horseradish peroxidase or alkaline phosphatase and, together with the unlabelled sample, is brought into contact with the corresponding antibody, whereon a second antibody is used to bind the first and radioactivity or the immobilized enzyme assayed (competitive assay); alternatively, thymosin β15 in the sample is allowed to react with the corresponding immobilized antibody, radioisotope- or enzyme-labelled anti-thymosin β15 antibody is allowed to react with the system and radioactivity or the enzyme assayed (ELISA-sandwich assay). Other conventional methods may also be employed as suitable.

The above techniques may be conducted essentially as a "one-step" or "two-step" assay. The "one-step" assay involves contacting antigen with immobilized antibody and, without washing, contacting the mixture with labeled antibody. The "two-step" assay involves washing before contacting the mixture with labeled antibody. Other conventional methods may also be employed as suitable.

Enzymatic and radio-labelling of thymosin β15 and/or the antibodies may be effected by conventional means. Such means will generally include covalent linking of the enzyme to the antigen or the antibody in question, such as by glutaraldehyde, specifically so as not to adversely affect the activity of the enzyme, by which is meant that the enzyme must still be capable of interacting with its substrate, although it is not necessary for all of the enzyme to be active, provided that enough remains active to permit the assay to be effected. Indeed, some techniques for binding enzyme are non-specific (such as using formaldehyde), and will only yield a proportion of active enzyme.

It is usually desirable to immobilize one component of the assay system on a support, thereby allowing other components of the system to be brought into contact with the component and readily removed without laborious and time-consuming labor. It is possible for a second phase to be immobilized away from the first, but one phase is usually sufficient.

It is possible to immobilize the enzyme itself on a support, but if solid-phase enzyme is required, then this is generally best achieved by binding to antibody and affixing the antibody to a support, models and systems for which are well-known in the art. Simple polyethylene may provide a suitable support.

Enzymes employable for labelling are not particularly limited, but may be selected from the members of the oxidase group, for example. These catalyze production of hydrogen peroxide by reaction with their substrates, and glucose oxidase is often used for its good stability, ease of availability and cheapness, as well as the ready availability of its substrate (glucose). Activity of the oxidase may be assayed by measuring the concentration of hydrogen peroxide formed after reaction of the enzyme-labelled antibody with the substrate under controlled conditions well-known in the art.

Other techniques may be used to detect thymosin β15 according to preference. One such technique is Western blotting (Towbin et at., *Proc. Nat. Acad. Sci.* 76:4350 (1979)), wherein a suitably treated sample is run on an SDS-PAGE gel before being transferred to a solid support, such as a nitrocellulose filter. Anti-thymosin β15 antibodies (unlabelled) are then brought into contact with the support and assayed by a secondary immunological reagent, such as labelled protein A or anti-immunoglobulin (suitable labels including $^{125}$I, horseradish peroxidase and alkaline phosphatase).

Samples for diagnostic purposes may be obtained from any number of sources. A sample obtained direct from the tumor, such as the stroma or cytosol, may be used to determine the metastatic potential of the tumor. It may also be appropriate to obtain the sample from other biological specimens, such as blood or urine. Such diagnosis may be of particular importance in monitoring progress of a patient, such as after surgery to remove a tumor. If a reference reading is taken after the operation, then another taken at regular intervals, any rise could be indicative of a relapse, or possibly a metastasis. Preferably, the sample is from the tumor itself.

The antibodies may be raised against either a peptide of thymosin β15 or the whole molecule. Such a peptide may be presented together with a carrier protein, such as an KLH, to an animal system or, if it is long enough, say 25 amino acid residues, without a carrier. Preferred peptides include regions unique to thymosin β15, such as amino acid 7 to 12 of SEQ ID NO: 2, amino acid 21 to 24 of SEQ ID NO: 2 and amino acid 36 to 45 of SEQ ID NO: 2.

Polyclonal antibodies generated by the above technique may be used direct, or suitable antibody producing cells may be isolated from the animal and used to form a hybridoma by known means (Kohler and Milstein, *Nature* 256:795. (1975)). Selection of an appropriate hybridoma will also be apparent to those skilled in the art, and the resulting antibody may be used in a suitable assay to identify thymosin β15.

This invention provides a convenient kit for measuring human thymosin β15 levels. This kit includes antibodies or antibody fragments which selectively bind human thymosin β15 or a set of DNA oligonucleotide primers that allow synthesis of cDNA encoding human thymosin β15. Preferably, the primers comprise at least 10 nucleotides and hybridizes under stringent conditions to a DNA fragment having the nucleotide sequence set forth in SEQ ID NO:1. As herein used, the term "stringent conditions" means hybridization will occur only if there is at least 95% and preferably at least 97% identity between the sequences.

DNA encoding human thymosin β15 and recombinant human thymosin β15 may be produced according to the methods set forth in copending application Express Mail No. TB338582343, the disclosure of which is incorporated herein.

All references cited above or below are herein incorporated by reference.

The following Examples serve to illustrate the present invention, and are not intended to limit the invention in any manner.

EXAMPLES

Methods

RT—PCR Analysis

Total RNA from each cell line was digested with RNase free DNase I (GIBCO BRL, Gaithersburg, Md.). DNase I digested 5 μg of total RNA was reverse transcribed using cDNA Cyling Kit (Invitrogen). The reverse transcription mixture was purified with a Spin Column 300 (Pharmocia, Piscataway, N.J.). 10 μl of purified cDNA was amplified with primer sets of Tβ15 forward primer:

5'-TATCAGCTAGTGGCTGCACCCGCG-3' (SEQ ID NO:3) and reverse primer: 5'-AAATGCTGACCTTTCAGTCAGGGT-3' (SEQ ID NO:4); Tβ4 forward primer: 5'-ACTCTCAATTCCACCA TCTCCCAC-3' (SEQ ID NO:5), reverse primer: 5'-GCCTCTGAGCAGATCGTCTCTCCTTG-3' (SEQ ID NO:6); and Tβ10 forward primer:

5'-ATAATATCCCTGGGCAAACCGGTG-3' (SEQ ID NO:7), reverse primer: 5'-GAGTGGAG TACCTGGAGCGCGAGC-3' (SEQ ID NO:8), respectively. PCR amplification was performed in 50 μl of PCR reaction-buffer (50 mM KCl, 10 mM Tris [pH 8.5], 1.5 mM MgCl$_2$)

with 1 mM of dNTPs, 50 pmol of each primer, and 2.5 U of Taq polymerase (GIBCO BRL), overlaid with 50 μl of mineral oil (Sigma). The PCR profile was 94° C., 30 sec; 60° C., 30 sec; and 72° C., 2 min for 30 cycles.

Control studies of the RT—PCR were conducted using aliquats from the same samples and amplified with primers to the β-actin gene (Clontech, Palo Alto, Calif.). Amplification products were separated on 1.4% agarose gels.

In situ hybridization

Antisense and sense Tβ15 mRNA probes were prepared using Tβ15 cDNA inserted into the eukaryotic expression vector pcDNA3 (Invitrogen) as template and a digoxigenin RNA labeling kit (Boehringer Mannheim). Formalin-fixed paraffin-embedded sections were dewaxed, rehydrated, and digested with proteinase K (50 μg/ml) in 100 mM Tris, 50 mM EDTA buffer (pH 8) for 8 min at 37° C. Hybridization was performed in an automated instrument (Ventana Medical Systems, Tuscon, Ariz.) for 60 min at 42° C. with 10 pM digoxigenin-labeled riboprobe in 100 μu of hybridization buffer (50% deionized formamide, 4×SSC, 10% dextran sulfate, 1% SDS, and denatured herring sperm DNA (400 μg/ml)) per section under a liquid cover slip. The highest stringency of posthybridization washes was at 45° C. for 15 min in 0.1×SSC. Bound digoxigenin-labeled probe was detected by anti-digoxigenin alkaline phosphatase conjugate and visualized by nitroblue tetrazolium and 5-bromo-4-chloro-3-indolylphosphate (NBT-BCIP) color reaction. Sections were counterstained with nuclear fast red.

Cell motility

Migration of transfectants was studied using a multiwell chamber assay as previously described (Kunda, et al., *J. Cell Biol.* 130, 725 (1995)) 48-well chemotaxis chambers were overlaid with 8-μm porosity polycarbonate filters (Nucleopore Corp., Pleasanton, Calif.) precoated with PBS containing 11.5 μg/ml fibronectin (Capple Organon Technica, Durham, N.C.). The migration of 5,000 cells placed in the upper well toward fetal bovine serum in the lower well was assayed following a 4 hour incubation at 37° C. After removal of cells from the upper side of the filters, cells that had passed through the filters and adhered to the lower side were fixed in formalin, washed with PBS and stained with Gill's triple strength hematoxylin (Polysciences, Warrington, Pa.) and counted under light microscopy.

Immunohistochemical staining

Human prostate cancer sections were studied using an immunoperoxidase ABC kit (Vector, Burlingame, Calif.). Briefly, the 5 μm tissue sections were deparaffinized in xylene, rehydrated in graded alcohols, and blocked for endogenous peroxidase by 3% hydrogen peroxide (Sigma) in methanol for 30 min. The sections were treated with normal goat serum for 30 min and then incubated with an affinity purified anti Tβ15 C-terminal peptide antibody for 2 h at room temperature at 1:100 (v/v) dilution, followed by incubation with a biotinylated goat anti-rabbit IgG antibody for 30 min. After incubation with a preformed ABC complex for 30 min, specifically bound antibodies were visualized by using peroxidase substrate, 3,3'-diaminobenzidine tetrahydrochloride (DAB). Sections were counterstained with Gill's hematoxylin.

Results

Cloning of Human Thymosin β15 by RT—PCR

DNase I digested 5 μg of total RNA from human prostatic carcinoma cell line PC-3 was reverse transcribed using cDNA Cycling Kit (Invitrogen). The reverse transcription mixture was purified with a Spin Column 300 (Pharmocia, Piscataway, N.Y.). 10 μl of purified cDNA reaction was amplified with primers F1

(5'-TATCAGCTAGTGGCTGCACCCGCG-3') (SEQ ID NO:8) and RI (5'-AAATGCT GACCTTTCAGTCAGGGT-3') (SEQ ID NO:9) designed to anneal to the outer ends of the thymosin β15 sequence. PCR amplification was performed in 50 μl of PCR reaction buffer (50 mM KCl, 10 mM Tris [pH 8.5], 1.5 mM MgCl2) with 1 mM of dNTPs, 50 pmol of each primer, and 2.5 U of Taq polymerase (GIBCO BRL), overlaid with 50 μl of mineral oil (Sigma). The PCR profile was 94° C., 30 sec; 60° C., 30 sec; and 72° C., 2 min for 30 cycles. Control studies of the RT—PCR were conducted using aliquats from the same samples and amplified with primers to the β-actin gene (Clontech, Palo Alto, Calif.). Amplification products were separated on 1.6% agarose gels. The amplified PCR product was ligated to pCR using TA cloning kit (Invitrogen, San Diego, (Calif.), and then DNA sequenced. The sequence of the PCR product of human prostatic carcinoma cells amplified by the thymosin β15 primers is set forth in FIG. 1 (SEQ ID NOS: 1 and 2).

Expression of Tβ15 mRNA in human prostate cancer

Figure 3B:
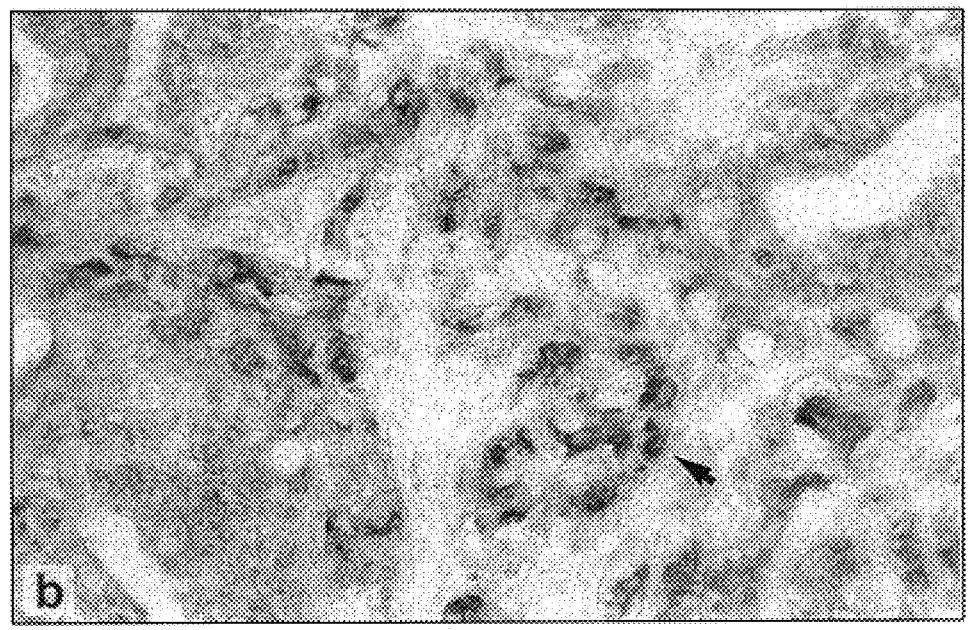

To determine whether this thymosin family member may be expressed in human prostate cancer, we examined human prostatic carcinoma cell line PC-3 by RT-PCR with forward and reverse primers for thymosin β15. The PC-3 cells showed a low level of thymosin β15 expression. The DNA sequence of the amplified PCR product was 100% identical to the rat thymosin β15 sequence. We conducted in situ hybridization study on samples from patients with varying grades of prostatic carcinomas using a thymosin β15 probe. The tissue sections allowed direct comparison of normal and malignant elements on the same samples. The stromal elements within and around the tumor cell masses, as well as the nonmalignant prostatic epithelium adjacent to the tumor showed little background hybridization with the thymosin β15 antisense probe. In contrast, specific tumor cell islands exhibited a strong specific thymosin β15 signal when probed with antisense (FIG. 3A, small arrow) but not with a sense RNA probe (data not shown). Although nearly all of the tumor cells in the positive islands expressed thymosin β15 mRNA, not all patient specimens were positive and not all islands in a single prostate were positive (FIG. 3A, large arrow). The majority of the negative tumor cells were in non-invasive in situ carcinomas whereas highly invasive tumors were consistently positive (FIG. 3B). Thus a novel β thymosin, first detected in metastatic rat prostate carcinoma cell lines, is upregulated in human prostate cancer.

Effect of Tβ15 on cell motility

Figure 4A:
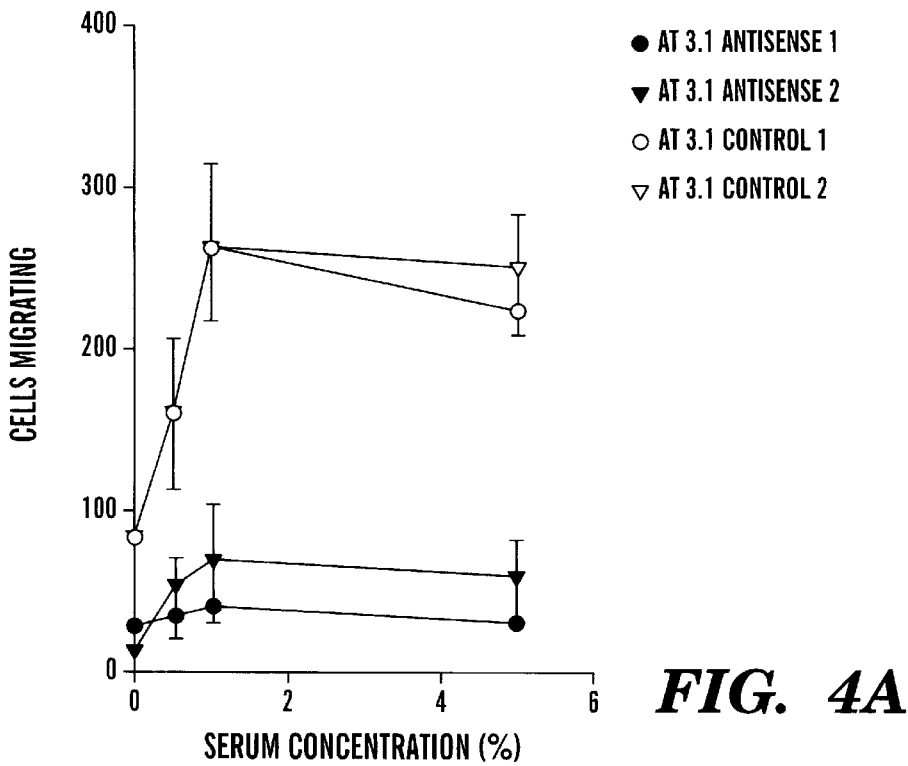
FIGS. 4A, 4B and 4C show serum stimulated migration of control transfected and Tβ15 transfected Dunning R-3327 variants and their growth rate.
Figure 4B:
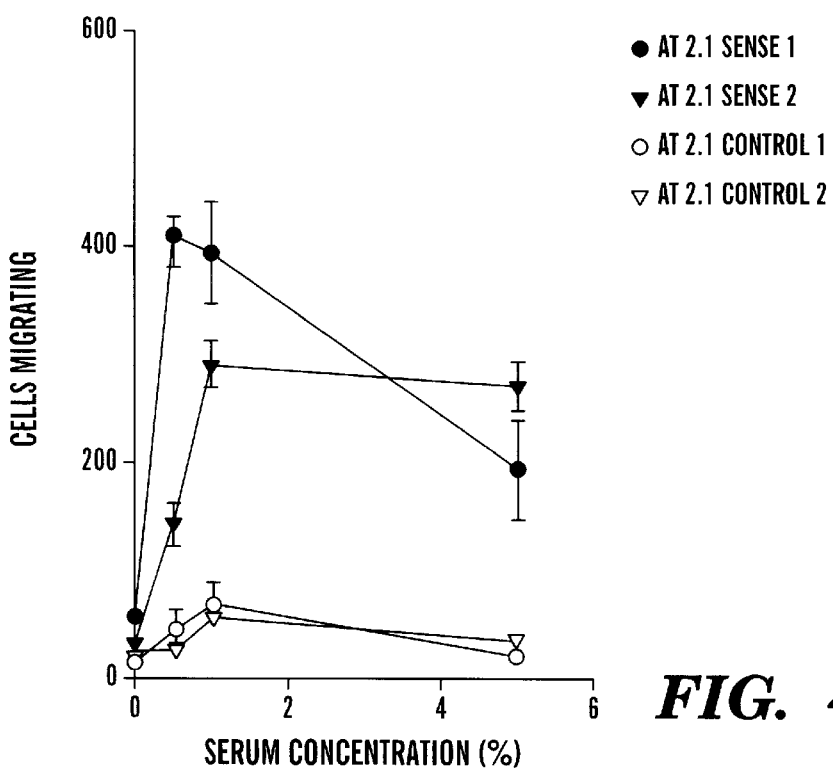
Figure 4C:
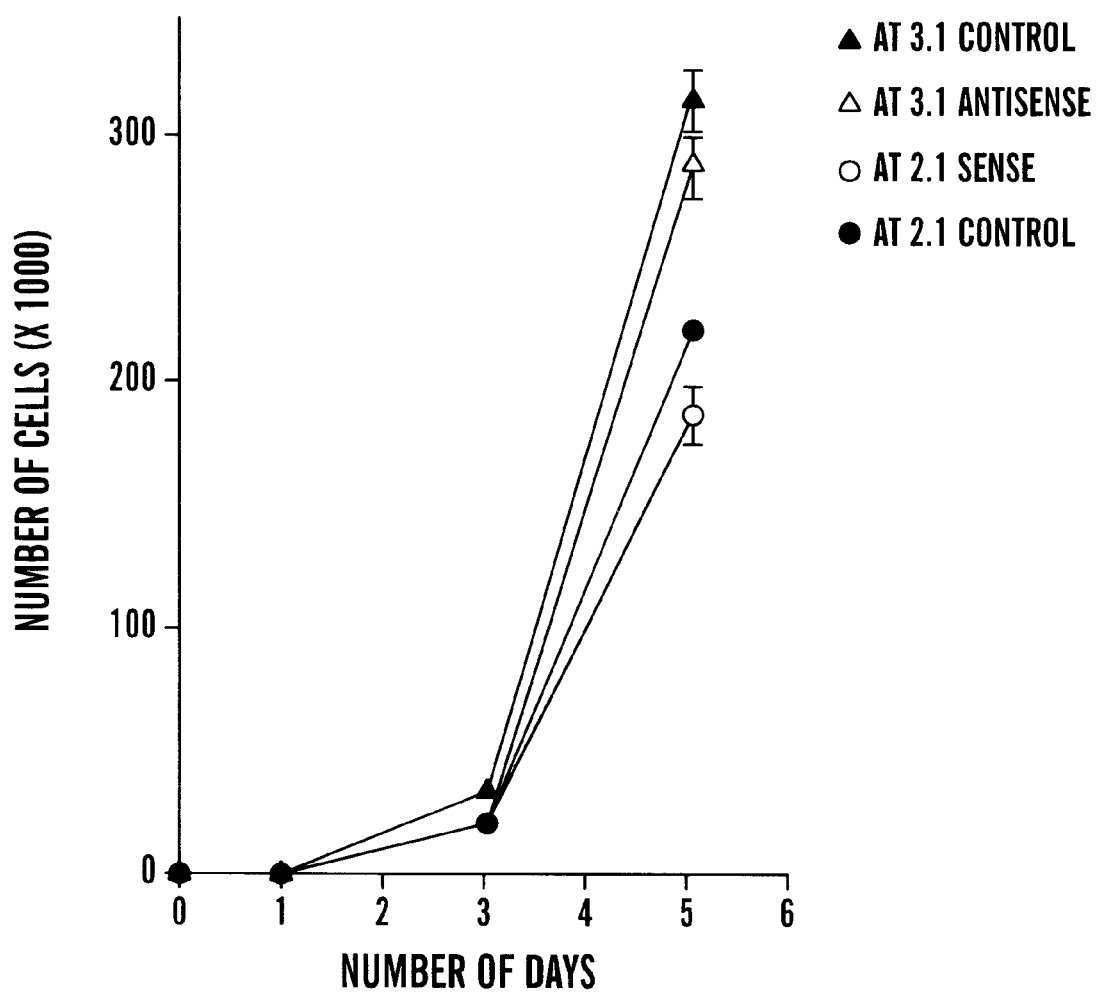

To determine whether thymosin β15 expression had an effect on cell motility, we transfected highly motile AT3.1 cells with a eukaryotic expression vector (pcDNA3) containing the thymosin β15 gene in antisense orientation driven by the constitutive human cytomegalovirus promoter. The transfected cells growing in selective (G418) media were examined for expression of antisense transcripts of the thymosin β15 gene by strand-specific polymerase chain reaction (PCR) amplification (Zhou, et al., *Cancer Res.* 52, 4280–4285 (1992)). Analysis of cell motility in a multiwell Boyden chamber apparatus (Boyden, S. V., *J. Exp. Med.* 115, 453–466 (1962)) using fetal bovine serum as a migration stimulus revealed that the motility of the transfectants which showed expression of antisense transcripts was significantly reduced relative to the vector-only controls (FIG. 4A). Two antisense transfected clones which did not express antisense transcripts failed to show any decreased rate of cell motility (data not shown). In a further experiment, poorly motile AT2.1 cells, transfected with sense thymosin β15 constructs and confirmed to express thymosin β15 by Northern analysis, were shown to have significantly increased stimulated motility relative to their vector controls (FIG. 4B). Both the sense and antisense thymosin β15 transfectants showed similar rates of cell proliferation relative to controls suggesting differential specificity for different cellular events (FIG. 4C). The results demonstrate that thymosin β15, which is upregulated in the highly motile AT3.1 and AT6.1 Dunning tumor cell lines, is a positive regulator of cell motility which is an important component of cancer metastasis.

Immunohistochemical detection of Tβ15 in prostate carcinoma

A polyclonal antibody was raised against a peptide representing the 11 C-terminal amino acids of thymosin β15. Synthesized peptide was coupled with a carrier, keyhole limpet hemocyanin (KLH), and injected into rabbits. Antiserum was affinity-purified over the C-terminal peptide coupled CNBr-activated sepharose 4B column. To test the specificity of the purified antibody, we performed Western analysis of the GST/thymosin β fusion proteins with the affinity-purified anti C-terminal antibody. The purified antibody strongly reacted with GST-thymosin β15 fusion protein, but did not cross react with GST-thymosin β4, and not with GST alone showing its specificity.

Figure 5A:
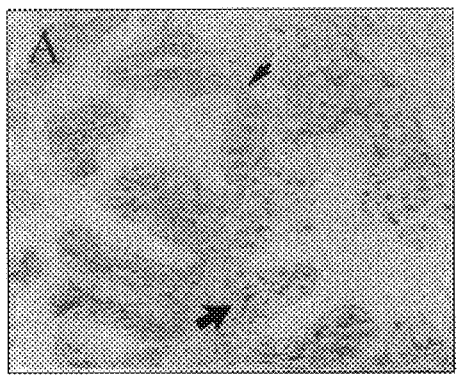
FIGS. 5A, 5B, 5C and 5D show immunohistochemical staining of human prostatic carcinoma tissues with an affinity purified polyclonal antibody to thymosin β15. A. Nonmalignant prostatic epithelia (large arrow) and high-grade prostatic intraepithelial neoplasia (PIN) (small arrow). B. Moderately differentiated prostatic carcinoma showing heterogeneous immunostaining (small arrow, positive; large arrow, negative). C. Poorly differentiated prostatic carcinoma. D. Single cells invading stroma showing intense staining.
Figure 5B:
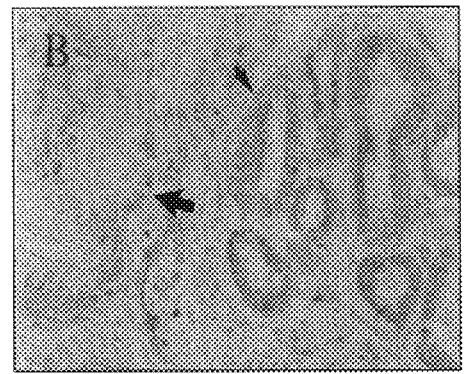
Figure 5C:
Figure 5D:
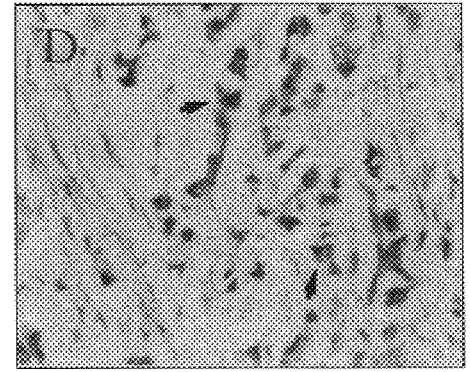

We used the affinity purified polyclonal thymosin β15 antibody for immunohistochemical study of human prostate carcinoma. The results are summarized below in Table 1. The thymosin β15 immunostaining was observed in the cytoplasms of epithelial cells in neoplastic prostates but not in normal prostates and not in the stromal cells (FIG. 5A, large arrow). Among the investigated malignant epithelia, the poorly differentiated prostate carcinomas displayed the most extensive and intense thymosin β15 immunoreaction (FIG. 5C), followed by moderately differentiated prostate carcinomas in which not all carcinomas expressed thymosin β15 showing partial positivity (FIG. 5B). In some cases, high-grade prostatic intraepithelial neoplasia (PIN) showed thymosin β15 immunostaining, but to a lesser extent (FIG. 5A, small arrow). In poorly differentiated invasive carcinoma, single cells invading stroma displayed intense staining (FIG. 5D). The expression of thymosin β15 well correlated with Gleason grade of prostate carcinoma.

TABLE 1

THYMOSIN β15 EXPRESSION IN HUMAN PROSTATE CARCINOMA

| Prostate | No. | Negative[a] | Partial[b] | Positive[c] |
|---|---|---|---|---|
| BPH | 2 | 2 | 0 | 0 |
| Ca Gleason 2~5 | 5 | 3 | 2 | 0 |
| Ca Gleason 6~8 | 25 | 4 | 7 | 14 |
| Ca Gleason 9~10 | 6 | 0 | 1 | 5 |
| Ca (with met) | 3 | 0 | 1 | 2 |

(BPH - Benign Prostate Hyperplasia; CA-Carcinoma)
[a]less than 10% cells showing positivity
[b]heterogeneous staining with 30~75% of cells showing positivity
[c]homogeneous staining with 75~100% of cells showing positivity This invention has been described in detail including the preferred embodiments thereof. However, it will be appreciated that those skilled in the art, upon consideration of this disclosure, may make modifications and improvements thereon without departing from the spirit and scope of the invention as set forth in the claims.

What is claimed is:

1. A method for diagnosing cancer in a patient comprising:
   (i) detecting in a first biological specimen thymosin β15 protein or thymosin β15 mRNA encoding thymosin β15, wherein said thymosin β15 comprises amino acids 36 to 45 of SEQ ID NO:2, and
   (ii) comparing the level of thymosin β15 protein or thymosin β15 mRNA in the first sample with a base line level determined by measuring thymosin β15 levels in disease free individuals, wherein levels of thymosin β15 mRNA greater in the first sample compared to the second is indicative of cancer.

2. The method of claim 1, wherein the biological specimen is selected from blood, tissue, serum, stool, urine, sputum, cerebrospinal fluid and supernatant from cell lysate.

3. The method of claim 1, wherein the level of mRNA expressing thymosin β15 is measured.

4. The method of claim 3, wherein the mRNA is detected by use of an RNA dependent polymerase chain reaction.

5. The method of claim 1, wherein the level of the thymosin β15 protein is measured.

6. The method of claim 3, wherein the mRNA is detected by Northern blot analysis by hybridizing mRNA from said biological specimen to a thymosin β15 nucleotide probe.

* * * * *

SEQUENCE LISTING (1) GENERAL INFORMATION:

(iii) NUMBER OF SEQUENCES: 8

(2) INFORMATION FOR SEQ ID NO:1:

(i) SEQUENCE CHARACTERISTICS:
      (A) LENGTH: 412 base pairs
      (B) TYPE: nucleic acid
      (C) STRANDEDNESS: single
      (D) TOPOLOGY: linear (ii) MOLECULE TYPE: cDNA (iii) HYPOTHETICAL: NO (iv) ANTISENSE: NO (v) FRAGMENT TYPE:

(vi) ORIGINAL SOURCE:

(ix) FEATURE:

(A) NAME/KEY: Coding Sequence
      (B) LOCATION: 98...232
      (D) OTHER INFORMATION: Exon 1

(xi) SEQUENCE DESCRIPTION: SEQ ID NO:1:

```
TATCAGCTAG TGGCTGCACC CGCGAACACC ACCCTGGTCC GGAGTAGCTG CGGACAGAAT        60

TGCTGGCCTA GTAGAAGCTT TGGAACGAGC AGTCAAG ATG AGT GAT AAA CCA GAC       115
                                         Met Ser Asp Lys Pro Asp
                                          1               5

TTA TCA GAA GTT GAA ACA TTT GAC AAA TCA AAG TTG AAG AAG ACT AAT        163
Leu Ser Glu Val Glu Thr Phe Asp Lys Ser Lys Leu Lys Lys Thr Asn
            10                  15                  20

ACT GAA GAA AAG AAT ACT CTT CCT TCG AAG GAA ACT ATC CAG CAG GAG        211
Thr Glu Glu Lys Asn Thr Leu Pro Ser Lys Glu Thr Ile Gln Gln Glu
            25                  30                  35

AAA GAA TAT AAT CAA AGA TC ATAAAATGAG ATTCTCCTCT CAAGAGCAAC TTCAAC     267
Lys Glu Tyr Asn Gln Arg Ser
            40              45

TTTGCTGGAT AGTCTTGGAT TTAGACATGT TTCTGTAAAC CTATCCAATA TGTAGACATT      327
TTAGGCGGTT CCTGATAGGT TCTTAAGTAC CCTGACTGAA AGGTCAGCAT TTAACACCAA      387
TCATTAAATG TGTTTTCCAC TGCTC                                            412

(2) INFORMATION FOR SEQ ID NO:2:

(i) SEQUENCE CHARACTERISTICS:
        (A) LENGTH: 45 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTISENSE: NO (v) FRAGMENT TYPE: internal (vi) ORIGINAL SOURCE:

(xi) SEQUENCE DESCRIPTION: SEQ ID NO:2:

Met Ser Asp Lys Pro Asp Leu Ser Glu Val Glu Thr Phe Asp Lys Ser
 1               5                  10                  15

Lys Leu Lys Lys Thr Asn Thr Glu Glu Lys Asn Thr Leu Pro Ser Lys
                20                  25                  30

Glu Thr Ile Gln Gln Glu Lys Glu Tyr Asn Gln Arg Ser
            35                  40              45

(2) INFORMATION FOR SEQ ID NO:3:
```

```
        (i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTISENSE: NO (v) FRAGMENT TYPE:

(vi) ORIGINAL SOURCE:

(xi) SEQUENCE DESCRIPTION: SEQ ID NO:3:

TATCAGCTAG TGGCTGCACC CGCG (2) INFORMATION FOR SEQ ID NO:4:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTISENSE: NO (v) FRAGMENT TYPE:

(vi) ORIGINAL SOURCE:

(xi) SEQUENCE DESCRIPTION: SEQ ID NO:4:

AAATGCTGAC CTTTCAGTCA GGGT                                             24

(2) INFORMATION FOR SEQ ID NO:5:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTISENSE: NO (v) FRAGMENT TYPE:

(vi) ORIGINAL SOURCE:

(xi) SEQUENCE DESCRIPTION: SEQ ID NO:5:

ACTCTCAATT CCACCATCTC CCAC                                             24
```

-continued (2) INFORMATION FOR SEQ ID NO:6:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTISENSE: NO (v) FRAGMENT TYPE:

(vi) ORIGINAL SOURCE:

(xi) SEQUENCE DESCRIPTION: SEQ ID NO:6:

GCCTCTGAGC AGATCGTCTC TCCTTG                        26

(2) INFORMATION FOR SEQ ID NO:7:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTISENSE: NO (v) FRAGMENT TYPE:

(vi) ORIGINAL SOURCE:

(xi) SEQUENCE DESCRIPTION: SEQ ID NO:7:

ATAATATCCC TGGGCAAACC GGTG                          24

(2) INFORMATION FOR SEQ ID NO:8:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTISENSE: NO (v) FRAGMENT TYPE:

(vi) ORIGINAL SOURCE:

(xi) SEQUENCE DESCRIPTION: SEQ ID NO:8:

GAGTGGAGTA CCTGGAGCGC GAGC                                    24